United States Patent [19]
Stone

[11] Patent Number: 6,008,433
[45] Date of Patent: Dec. 28, 1999

[54] OSTEOTOMY WEDGE DEVICE, KIT AND METHODS FOR REALIGNMENT OF A VARUS ANGULATED KNEE

[76] Inventor: Kevin R. Stone, 1 Throckmorton La., Mill Valley, Calif. 94941

[21] Appl. No.: 09/064,958

[22] Filed: Apr. 23, 1998

[51] Int. Cl.$^6$ ...................................................... A61F 2/28
[52] U.S. Cl. .................................. 623/16; 606/61; 623/20
[58] Field of Search .................................. 623/16, 17, 18, 623/20; 433/175; 606/60, 61, 70, 74, 88

[56] References Cited

U.S. PATENT DOCUMENTS

| | | | |
|---|---|---|---|
| 4,199,864 | 4/1980 | Ashman | 433/175 |
| 4,484,570 | 11/1984 | Sutter et al. | 128/92 |
| 4,746,532 | 5/1988 | Suzuki et al. | 427/2 |
| 5,047,058 | 9/1991 | Roberts et al. | 623/20 |
| 5,108,399 | 4/1992 | Eitenmuller et al. | 606/77 |
| 5,129,904 | 7/1992 | Illi | 606/72 |
| 5,192,327 | 3/1993 | Brantigan | 623/17 |
| 5,306,307 | 4/1994 | Senter et al. | 623/17 |
| 5,306,309 | 4/1994 | Wagner et al. | 623/17 |
| 5,364,400 | 11/1994 | Rego, Jr. et al. | 606/72 |
| 5,716,415 | 2/1998 | Steffee | 623/17 |
| 5,766,251 | 6/1998 | Koshino | 623/16 |
| 5,865,847 | 2/1999 | Kohrs et al. | 623/17 |

FOREIGN PATENT DOCUMENTS

| | | | |
|---|---|---|---|
| 60-150756 | 8/1985 | Japan | 623/16 |
| 4-055266 | 5/1993 | Japan | 623/16 |
| 1107854 | 8/1984 | U.S.S.R. | 623/17 |

OTHER PUBLICATIONS

Frank R. Noyes et al., High Tibial Osteotomy in Knees with Associated Chronic Ligament Deficiencies, *Master Techniques in Orthopaedic Surgery,* Reconstructive Knee Surgery, 185–210, (1995).

A. Miniaci et al., Proximal Tibial Osteotomy, A New Fixation Device, No. 246, *Clinical Orthopaedics and Related Research,* 250–259, (Sep. 1989).

James J. Elting, M.D. et al., Unilateral Frame Distraction: Proximal Tibial Valgus Osteotomy for Medical Gonarthritis, vol. 27, No. 5, *Contemporary Orthopaedics,* 435–440, (Nov. 1993).

Dr. Ch. Mansat, The Mansat Staple Blade, Sales brochure from Societe De Protheses Othopedie Reeducation Traumatologie, Saint–Jean 31240 France.

*Primary Examiner*—Bruce E. Snow
*Attorney, Agent, or Firm*—Lappin & Kusmer LLP

[57] ABSTRACT

The invention provides an osteotomy device, and kit and methods for realigning varus angulated knees. The device involves a substantially wedge-shaped body having two intersecting principal surfaces angularly offset. These principal surfaces extend in a direction of a drive axis about a principal plane from an insertion end to a drive surface at a drive end. At least one of the principal surfaces is adapted to engage mechanically a surface adjacent thereto. The drive surface is also adapted to receive a force in the direction of the drive axis toward the insertion end. The kit of the present invention includes substantially such an osteotomy device having cannular opening along its drive axis and an osteotomy pin. A method of the invention involves making a transverse incision partially into the tibia; realigning tibial portions above and below the incision with respect to each other to create a predetermined angle A between opposing faces of the incision, thereby creating a wedge-shaped opening; providing a substantially wedge-shaped body having two angularly offset intersecting principal surfaces, wherein at least one of the surfaces is adapted to engage mechanically a surface adjacent thereto; and driving the body into the opening. Another invention method involves making the incision and realigning the tibia substantially as described above followed by positioning an osteotomy pin within the wedge-shaped opening; and placing the substantially wedge-shaped body having a cannular opening along a drive axis within the wedge-shaped opening such that the pin is positioned in the cannular opening of the body.

19 Claims, 4 Drawing Sheets

LATERAL ↔ MEDIAL

LATERAL ←→ MEDIAL

OSTEOTOMY WEDGE DEVICE, KIT AND METHODS FOR REALIGNMENT OF A VARUS ANGULATED KNEE

FIELD OF THE INVENTION

The present invention relates to a device, a kit and methods for tibial realignment, and in particular, to a device, a kit and methods for the correction of varus angulated knees including the genu varus and genus valgus conditions.

BACKGROUND OF THE INVENTION

Varus angulated knees are deformities which are characterized by abnormal angulations of the leg in relation to the thigh. *Stedman's Medical Dictionary*, Williams & Wilkins, Baltimore, Md. (1995). For example, the genu varus angulated knee condition is characterized by an outward bowing of the legs and is commonly referred to as bowleg. Another example, the genu valgus angulated knee condition, is characterized by a lateral angulation of the leg in relation to the thigh and is commonly referred to as knock-knee. Either of these conditions may result in abnormal loads on the femurtibial joint. Further, such loads may cause tensile forces to develop in the collateral ligaments and other soft tissue structures. Persons with varus angulated knee conditions may experience knee pain, swelling, recurrent loss of stability related to activity, functional limitations, and subluxation. Both the genu varus and genu valgus angulated knee conditions may require reconstruction of the surrounding ligaments as well as correction of the abnormal angulation.

High Tibial Osteotomies (HTO) are surgical methods used to correct the abnormal angulations of varus angulated knees. Frank R. Noyes, et al., *High Tibial Osteotomy in Knees with Associated Chronic Ligament Deficiencies* in Master Techniques in Orthopaedic Surgery, Reconstructive Knee Surgery, 185, 185–187 (1995). In accordance with such methods, the desired angle of correction is first determined. Transverse and oblique incisions are then made into a lateral portion of the upper tibia forming a triangular-shaped opening. The opening is closed by rotating the lower portion of the tibia relative to the upper portion of the tibia so that the long axes of the lower and upper portions of the tibia are substantially aligned or slightly (e.g., 5–13 degrees valgus) over-corrected relative to the desired correction angle. A. Miniaci et al., *Proximal Tibial Osteotom. A New Fixation Device*, 246 Clinical Orthopaedics and Related Research 250, 250–259 (September 1989). The closure is secured with an L-shaped bracket or buttress that is screwed into the tibia on each side of the closure.

Accordingly, the HTO procedure requires shortening of the tibia and the fibula. Such shortening may lead to ankle pain. Additional incisions may also be necessary because it may be difficult to determine the amount of bone removal required.

Unilateral frame distraction procedures are alternative surgical methods for the correction of abnormal angulation of varus angulated knees. In accordance with such methods, the medial cortex of the tibia is divided leaving the medullary bone, the lateral aspect of the joint, the tibia and the peroneal nerve intact. James J. Elting, M.D. et al., *Unilateral Frame Distraction: Proximal Tibial Valgus Osteotomy for Medial Gonarthritis.* Vol. 27 No. 5 Contemporary Orthopaedics 435, 436 (1993). Pins or screws are placed, respectively, transversely into the proximal tibia epiphysis and into the mid-shaft region of the tibia, and used to attach the axial fixator. The purpose of the fixator is to distract the bone in order to position the tibia in the proper alignment. After surgery, the patient distracts the fixator approximately 1 millimeter per day (0.25 mm, 3 to 4 times per day) until the tibia is in the proper alignment and knee pain is relieved. Once callus formation occurs, the fixator is dynamized to encourage film bone consolidation. When the newly-formed medially based bone wedge appears mature and fully consolidated, the fixator is removed.

In contrast to one-time surgeries, the above-identified procedure may require approximately an additional three-month post-surgery distraction period to complete the correction, as well as removal of the fixator after that period. Further, during the post-surgery distraction period, the procedure may require active patient participation which may or may not be reliable. Moreover, the patient's wearing of the externally attached fixator may be cumbersome and embarrassing for the patient. In addition, whether the tibial realignment remains stable over time is not yet known.

Another surgical method for the correction of varus angulated knees involves a spacer attached to a blade plate. Dr. Ch. Mansat, *The Mansat Staple Blade*, Sales brochure from Societe De Protheses Othopedie Reeducation Traumatologie, Saint-Jean 31240 France. In accordance with this method, a transverse incision is made in the medial to lateral direction in the upper, medial portion of the tibia leaving the lateral cortex portion of the tibia intact. The lower portion of the tibia below the incision is positioned at a pre-determined angle to correct the varus deformity, with the intact lateral cortex of the tibia acting as a hinge. Angularly positioning the lower tibia portion separately from the upper portion of the tibia above the incision forms a triangular-shaped opening at the incision point. A square-shaped spacer attached to a blade plate is positioned in the mouth of the opening and secured with screws through the blade plate into the tibia.

In the above-identified method, a significant amount of bone growth is required to fill the opening, since the spacer has a different shape from the triangular-shaped opening formed by the surgical incisions. Further, once the spacer is properly positioned, the surgical method requires the additional step of fixing the screws of the blade plate into the tibia to secure the spacer to the bone.

Thus, there is a need for devices, kits and methods to correct varus angulated knee deformities which avoid shortening the tibia and fibula causing ankle pain. Further there is a need for devices, kits and methods which do not require the wearing of external devices and lengthy post-surgery correction periods involving potentially unreliable active patient participation. In addition, there is a need for devices and kits and methods that both promote bone growth and minimize the amount of bone growth required for correction and strengthening. Further, there is a need for varus angulated knee correction devices which are secured in the desired positions without the need for additional securing structures.

SUMMARY OF THE INVENTION

The foregoing and other objects are achieved by the invention which is directed to an osteotomy device, and kit and methods for realigning varus angulated knees, but also may be used for realigning any malaligned bone. In particular, the osteotomy devices and kits of the invention involve substantially wedge-shaped bodies having, inter alia, principal surfaces adapted to engage mechanically surfaces such as bone, thereby promoting contiguous bone formation and growth of bone cells around and attaching to the osteotomy devices.

The methods of the invention involve, inter alia, realigning portions of the tibia at a predetermined angle A to create a wedge-shaped opening; providing a substantially wedge-shaped body having two principal surfaces angularly offset by an angle A and extending to form vertex, wherein at least one of the surfaces is adapted to engage mechanically a surface adjacent thereto; and driving the body into the wedge-shaped opening. Alternatively, the methods of the invention involve, inter alia, additionally positioning an osteotomy pin within the wedge-shaped opening along a drive axis such that the pin extends radially outward from the tibia and placing the substantially wedge-shaped body having a cannular opening into the wedge-shaped opening along the drive axis such that the pin is positioned in the cannular opening of the body.

Accordingly, the device, kit and methods of the invention avoid shortening of the tibia and the fibula, the need for external correction devices and lengthy post-surgery correction procedures requiring active patient participation.

In one embodiment, the osteotomy device of the present invention involves a substantially wedge-shaped body having two principal surfaces which are angularly offset by an angle A and intersect to form a vertex. These surfaces extend at least in part about a principal plane from the vertex at an insertion end to a drive surface at a drive end. The principal plane contains a drive axis extending from the vertex toward the drive surface. The drive surface extends at least in part transversely to the principal plane. At least one of the principal surfaces is adapted to engage mechanically an adjacent surface, such as bone material. The drive surface is adapted to receive a force in the direction of the drive axis toward the insertion end.

In another embodiment, the invention provides a kit having substantially the above-identified osteotomy device, wherein the substantially wedge-shaped body has a portion defining a cannular opening along a drive axis extending from the vertex in the principal plane, and an osteotomy pin for placement within the cannular opening.

In yet another embodiment, the invention provides a method for realigning a varus angulated knee. The method involves making a transverse incision into the medial upper tibia, thereby creating a lower portion of the tibia capable of being realigned and leaving intact the lateral portion of the tibia; realigning the lower portion of the tibia at a predetermined angle A, thereby creating a wedge-shaped opening capable of receiving a substantially wedge-shaped body having two principal surfaces angularly offset by the predetermined angle A and intersecting to form a vertex, wherein at least one of the surfaces is adapted to engage mechanically a surface adjacent thereto; and driving the body into the wedge-shaped opening.

In still another embodiment, the invention provides a method for realigning a varus angulated knee. The method involves making a transverse incision into the medial upper tibia, thereby creating a lower portion of the tibia capable of being realigned and leaving intact the lateral portion of the tibia; realigning the lower portion of the tibia to a predetermined angle A, thereby creating a wedge-shaped opening capable of receiving a substantially wedge-shaped body having a portion defining a cannular opening between two principal surfaces angularly offset by the predetermined angle A and intersecting to form a vertex, wherein at least one of the surfaces is adapted to engage mechanically a surface adjacent thereto; positioning an osteotomy pin within the wedge-shaped opening along a drive axis such that the osteotomy pin extends radially outward from the intact tibial portion; and placing the substantially wedge-shaped body within the wedge-shaped opening along the drive axis such that the osteotomy pin is positioned in the cannular opening of the portion of the substantially wedge-shaped body.

BRIEF DESCRIPTION THE DRAWINGS

The foregoing and other objects of this invention, the various features thereof, as well as the invention itself, may be more fully understood from the following description, when read together with the accompanying drawings in which.

Figure 5A:
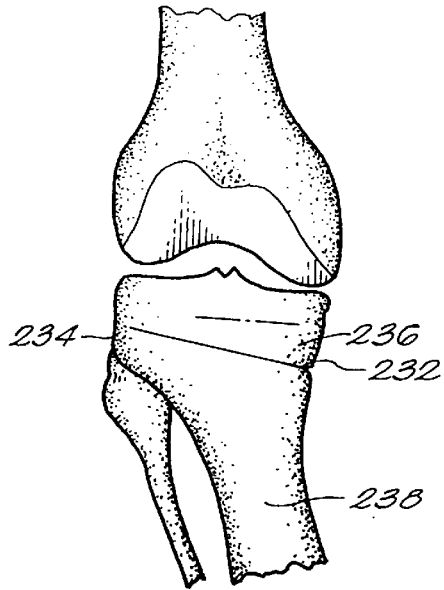
FIG. 5A illustrates a transverse incision into the medial upper tibia, according to an embodiment of the invention.
Figure 5B:
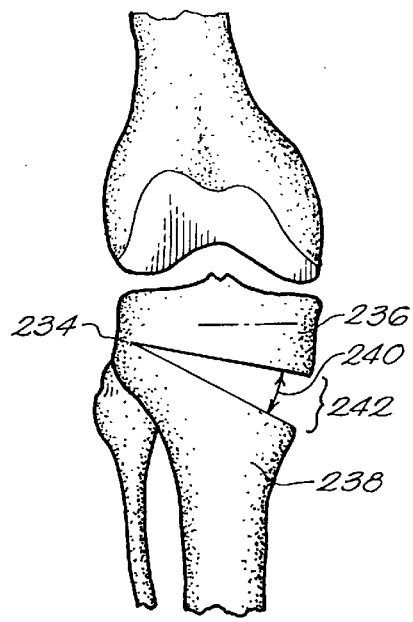
FIG. 5B illustrates the portion of the tibia below the transverse incision illustrated in FIG. 5A realigned at a predetermined angle, thereby creating an opening capable of receiving a substantially wedge-shaped body, according to an embodiment of the invention.
Figure 5C:
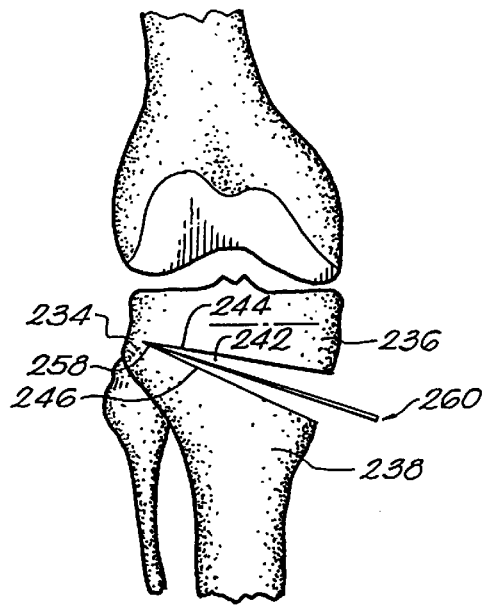
Figure 5D:
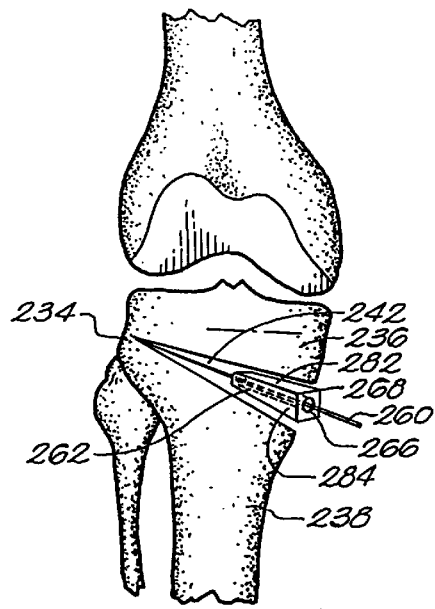

FIG. 5C illustrates an osteotomy pin positioned within the opening illustrated in FIG. 5B, according to an embodiment of the invention; and FIG. 5D illustrates a substantially wedge-shaped body having a cannular opening along a drive axis being placed within the opening along the drive axis illustrated in FIGS. 5B and 5C such that the osteotomy pin is positioned in the cannular opening of the substantially wedge-shaped body, according to an embodiment of the invention.

DETAILED DESCRIPTION THE INVENTION

The present invention provides an osteotomy device, kit and methods for realigning varus angulated knees. The osteotomy device of the present invention involves a substantially wedge-shaped body having, inter alia, a principal surface adapted to engage mechanically a surface, such as bone. The kit of the present invention includes such a substantially wedge-shaped body having a cannular opening along a drive axis, and an osteotomy pin for placement within the body's cannular opening. The method of the invention includes the steps of, inter alia, making a transverse incision partially into the tibia; realigning the portion of the tibia below the incision at a predetermined angle A between opposing faces of the incision thereby creating a wedge-shaped opening; providing a correspondingly substantially wedge-shaped body having two angularly offset intersecting principal surfaces, wherein at least one of the surfaces is adapted, at least in part, to engage mechanically a surface adjacent thereto; and driving the body into the wedge-shaped opening such that the body is mechanically held in place between the opposing faces and fills at least a part of a region between the opposing faces. Another method of the invention substantially includes the first two steps described above followed by the steps of, inter alia, positioning an osteotomy pin within the wedge-shaped opening and placing the substantially wedge-shaped body having a cannular opening along a drive axis within the opening along the body's drive axis such that the osteotomy pin is positioned in the body's cannular opening.

Figure 1A:
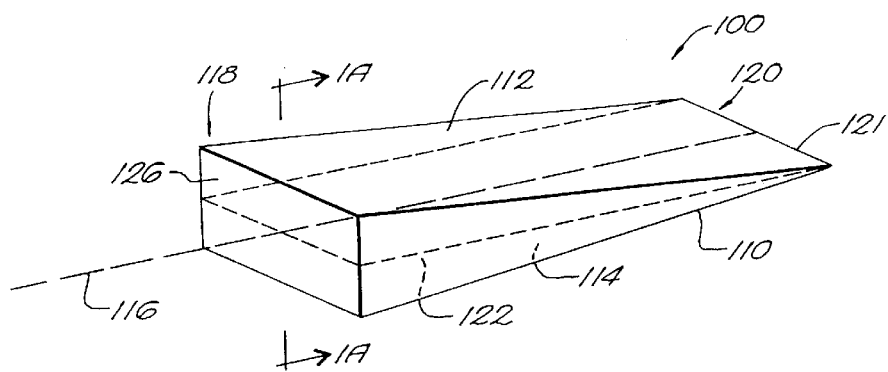
FIG. 1A illustrates a perspective view of an osteotomy device having a substantially wedge-shaped body, according to an embodiment of the invention.
Figure 1B:
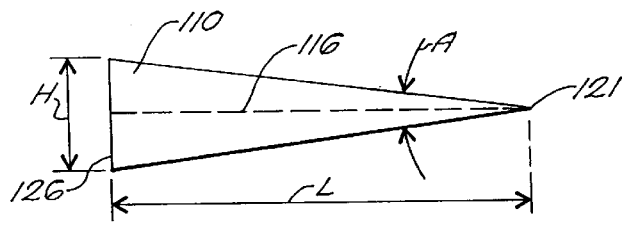
FIG. 1B illustrates in section, the device of FIG. 1A, along lines 1A—1A.

In one embodiment, the invention provides an osteotomy device 100, as shown in FIGS. 1A, 1B, 2A, 2B and 3A–3C. The device has a substantially wedge-shaped body 110 having two angularly offset intersecting principal surfaces 112, 114. The principal surfaces 112,114 intersect at a vertex 121 at insertion end 120 and in the illustrated embodiment, extend about a principal plane 122 extending midway between surfaces 112, 114 from the vertex 121 at the insertion end 120 to a drive surface 126 at a drive end 118. The principal plane 122 contains a drive axis 116. The drive surface 126 extends, at least in part, in a direction transverse to the principal plane 122. The drive surface 126 is adapted to receive a force in the direction of the drive axis 116 towards the insertion end 120. In the embodiment of FIGS. 1A–1B, the principal surfaces 112, 114 are planar and smooth. In other embodiments, different forms and surface textures of the principal surfaces 112, 114 can be used, as, for example, to assist in maintaining placement of the device 110 between two bone portions. For example, the osteotomy device of the present invention can be, at least in part, curved instead of planar. Alternative surface textures which can be used for surfaces 112, 114 are described in detail below. By way of example, the osteotomy devices of the present invention can be formed of materials manufactured by Bionix Implants, Inc., Blue Bell, Pa.

The dimensions of the osteotomy device 100 illustrated in FIG. 1A are shown in FIG. 1B. Preferably, the length (L) of the substantially wedge-shaped body 110 ranges from about 20 mm to about 100 mm, and more preferably ranges from about 30 mm to about 90 mm, most preferably ranges from about 40 mm to about 80 mm. The height (H) of the drive surface 126 of the substantially wedge-shaped body 110 ranges from about 4 mm to about 20 mm, and more preferably ranges from about 8 mm to about 15 mm. The angle (A) between surfaces 112, 114 of the substantially wedge-shaped body 110 ranges from about 5 degrees to about 25 degrees, and more preferably ranges from about 10 degrees to about 20 degrees.

At a minimum, at least one of the principal surfaces 112, 114 is adapted, at least in part, to engage mechanically a surface or surfaces thereto. The entire body 110 as a whole can be similarly adapted, however. For exemplary purposes, such adaptations are explained below in the context of principal surfaces 112, 114. Preferably, both surfaces 112, 114 are adapted, at least in part, to engage mechanically surfaces adjacent thereto. Thus, bone cells grow at the boundary of the exposed bone and the principal surfaces 112, 114 of the osteotomy device of the present invention. Such bone cells attach to the principal surfaces 112, 114 and secure the device's substantially wedge-shaped body to the osteotomy site.

In particular, the shapes, surface textures and/or materials of the principal surfaces 112, 114 are adapted to mechanically engage adjacent surface materials such as bone. For example, the substantially wedge-like shapes of the principal surfaces 112, 114 are designed to conform to the shape of an opening in the tibia where the body 110 is inserted. Thus, the principal surfaces 112, 114 substantially engage the walls of the tibial opening promoting bone growth to the principal surfaces 112, 114 and minimizing void space between the body 110 and the walls of the tibial opening.

Figure 2A:
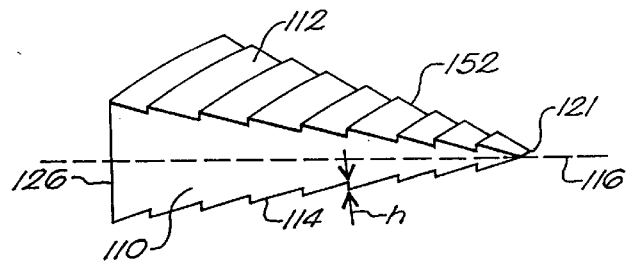
FIG. 2A illustrates the surface texture of the principal surface of a substantially wedge-shaped body of an osteotomy device having a saw-tooth contour on the principal surfaces, according to an embodiment of the invention.

In another exemplary embodiment, as shown in FIG. 2A, the saw-tooth surface textures of the principal surfaces 112 and 114 are adapted to mechanically engage surfaces adjacent to body 110. The saw-tooth contour of the surface textures defines uneven gradations 152 which increase the surface area available for bone adhesion. Preferably, the height (h) of each of the saw-tooth graduations ranges from about 1 mm to about 2 mm and more preferably, h is about 1.5 mm.

In still other exemplary embodiments, one or both of the principal surfaces 112, 114 are formed of a material selected to engage mechanically surfaces adjacent to body 110. By way of example, the principal surface 112 can be formed of a porous material which allows bone cells to grow within and throughout the pores. The diameters of such pores can range in size from about 50 micrometers to about 500 micrometers. Nonlimiting examples of such a porous material include polylactic acid (PLA), polyglycolic acid (PGA) and collagen.

In alternative embodiments, the material of one or both of the principal surfaces 112, 114 includes roughened non-porous material which has properties which facilitate the binding of bone to the principal surfaces 112, 114. Non-limiting examples of such a non-porous material include titanium, graphite, and steel. Other non-porous materials known to those of ordinary skill in the art to facilitate the binding of bone to the material can also be used to form the body 110 of the present invention.

In a further embodiment, the material of one or both of the principal surfaces 112, 114 is a resorbable material, such as lactides and collagen. Such resorbable material is absorbed into the recipient body as the bone cells develop throughout the osteotomy site. The resorbable material can be selected such that the substantially wedge-shaped body is absorbed into the recipient body over a predetermined time period. This predetermined time period can range from about 3 months to about 48 months. Non-limiting examples of a resorbable material which can be used to form the body 110 of the present invention include PLA, PGA, collagen and hydroxy apetite. Other resorbable materials known to those of ordinary skill in the art can also be used to form the body 110 of the present invention.

Figure 2B:
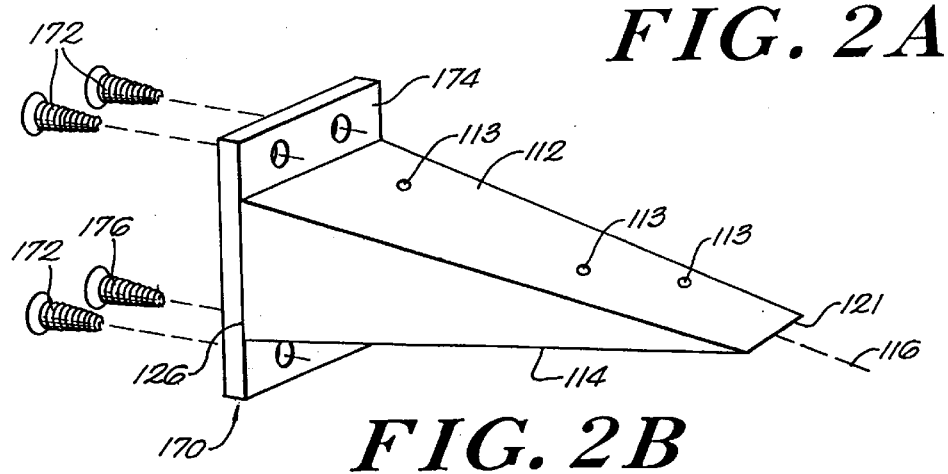
FIG. 2B illustrates an osteotomy device according to an embodiment of the invention, including a plate and screw system for securing the substantially wedge-shaped body of the osteotomy device to cortical and cancellous bone.

In still a further embodiment, the substantially wedge-shaped body 110 can be further secured with a screw and plate system 170, as illustrated in FIG. 2B. Screws 172 can be screwed through plate 174 and into the body 110.

Additional screws 176 can be screwed through the plate 174 and through the cortical bone into the cancellous bone. Screws 172 have sufficient length to reach opposite cortex. Preferably, screws 172, 176 have diameters ranging from about 4.5 mm to about 6.5 mm and lengths ranging from about 20 mm to about 100 mm, and more preferably from about 30 mm to about 90 mm, most preferably from about 40 mm to about 80 mm.

In yet another embodiment, the body 110 of the osteotomy device of the present invention can be hollow. Accordingly, materials such as ground cancellous bone can be packed within the body 110. Further, such a body 110 include a plurality of holes on the principal surface which can facilitate packing of material within the body 110.

Figure 3A:
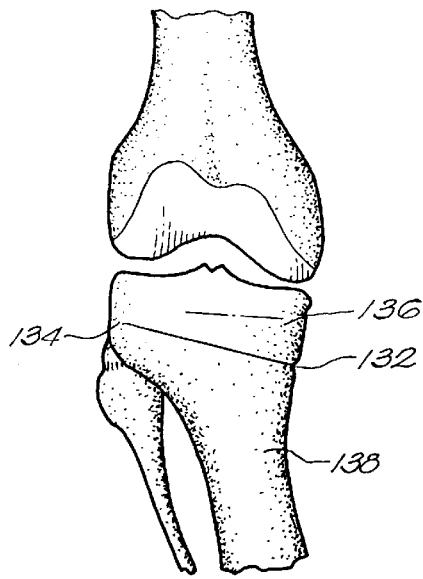
FIG. 3A illustrates a transverse incision into the medial upper tibia, according to an embodiment of the invention.
Figure 3B:
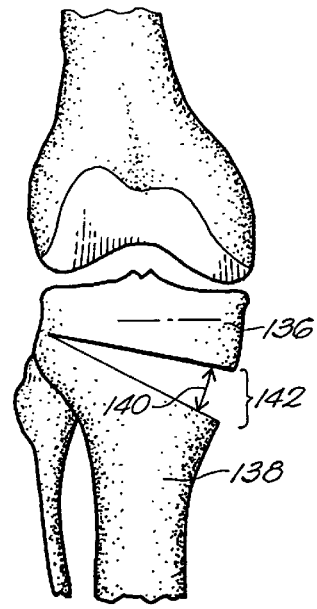
FIG. 3B illustrates the portion of the tibia below the transverse incision illustrated in FIG. 3A realigned at a predetermined angle, thereby creating an opening capable of receiving a substantially wedge-shaped body, according to an embodiment of the invention.
Figure 3C:
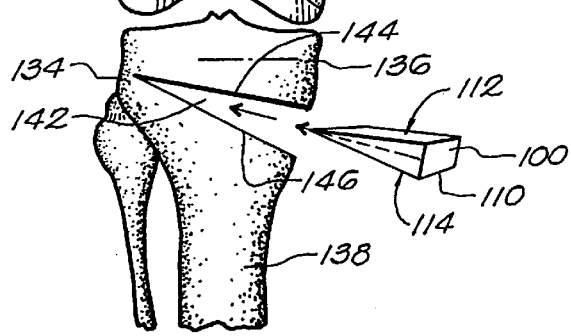
FIG. 3C illustrates a substantially wedge-shaped body driven into the opening illustrated in FIG. 3B, according to an embodiment of the invention.

FIGS. 3A–3C illustrate the steps of a method of the present invention for realigning a varus angulated knee. In accordance with this method, a transverse incision 132 is partially made into the tibia 136, as shown in FIG. 3A. Upper 136 and lower 138 portions of the tibia are created leaving the lateral portion 134 of the tibia intact. The upper 132 and lower 138 portions of the tibia are realigned with respect to each other to create predetermined angle 140 between opposing faces 144, 146 of the incision, thereby creating a substantially wedge-shaped opening 142, as shown in FIG. 3B. A correspondingly substantially wedge-shaped body having two principal surfaces angularly offset by the predetermined angle 140 and intersecting to form a vertex is provided. At least one of the principal surfaces is adapted, at least in part, to engage mechanically a surface adjacent thereto. Axial force is applied to the substantially wedge-shaped body to drive the body into the wedged-shaped opening 142.

In an embodiment of this method of the invention, the substantially wedge-shaped body consists of the substantially wedge-shaped body 110 of osteotomy device 100 described above, as illustrated in FIG. 3C. At least one of the principal surfaces 112, 114 of the osteotomy device 100 mechanically engages adjacent bone material facilitating adherence of the osteotomy device 100 to the osteotomy site. The substantially wedge-shaped form of the body 110 conforms substantially to the wedge-shaped surgical opening 142 in the tibia and thus minimizes the void space between the body 110 and the opposing faces 144, 146 defining the opening 142. Accordingly, the bone growth needed to fill such void space to secure the body 110 to the insertion site and to strengthen the realigned knee is minimized.

In still other embodiments of this method of the invention, cancellous bone is packed into between the body and the region between the opposing faces of the incision. Further, additional cancellous bone can be packed inside the body where the body is hollow. Such packing is facilitated where the body includes holes on its principal surface. Preferably the diameters of such holes can range from about 2 mm to about 10 mm.

Figure 4A:
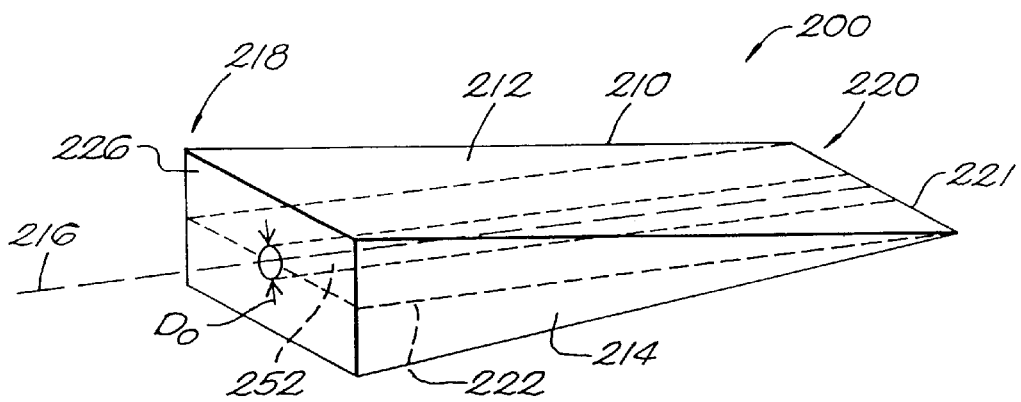
FIG. 4A illustrates a kit for realigning a varus angulated knee having, inter alia, a substantially wedge-shaped body having a cannular opening along a drive axis, according to an embodiment of the invention.

The invention further provides another osteotomy device 200 for realigning a varus angulated knee, as illustrated in FIG. 4A. The osteotomy device 200 includes a substantially wedge-shaped body 210 having two principal surfaces 212, 214 angularly offset and intersecting to form a vertex 221. The principal surfaces 212, 214 extend in the direction of a drive axis 216 about a principal plane 222 from the vertex 221 at an insertion end 220 to a drive surface 226 at a drive end 218. The principal plane 222 contains the drive axis 216. The drive surface 226 extends at least in part in a direction transverse to the principal plane 222. The drive surface 226 is adapted to receive a force in the direction of the drive axis 216 toward the insertion end 220.

At a minimum, at least one of the principal surfaces 212, 214 or at a maximum, the body 210 as a whole is adapted, at least in part, to engage mechanically a surface adjacent thereto. For example, the shapes, surface textures or materials of the principal surfaces 212, 214 or the body 210 as a whole are adapted, at least in part, to engage mechanically adjacent surface materials such as bone, as described above in relation to the osteotomy device 100. Preferably, both surfaces 212, 214 are adapted, at least in part, to engage mechanically surfaces adjacent thereto. Further, in the illustrated embodiment of FIG. 4A, the surfaces 212, 214 are planar. In other embodiments, other forms of the principal surfaces 212, 214 are possible. For example, the principal surfaces 212, 214 can be, at least in part, curved.

The substantially wedge-shaped body 210 also has a cannular opening 252 extending along drive axis 216. Preferably, the cannular opening 252 has a diameter (Do) ranging from about 1 mm to about 4 mm, and more preferably from about 2 mm to about 3 mm.

The height and length and angle of the substantially wedge-shaped body 210 of the osteotomy device 200 are substantially the same as the corresponding dimensions of the substantially wedge-shaped body 110 of the osteotomy device 100 described above and illustrated in FIG. 1B.

The diameter and length and angle of the body 210 of the osteotomy device 200 are substantially the same as the corresponding dimensions of the body 110 of the osteotomy device 100 described above and illustrated in FIG. 1B. Moreover, like the body 110 described above, the body 210 can be hollow and further, can include holes on the principal surface, as discussed above.

Figure 4B:
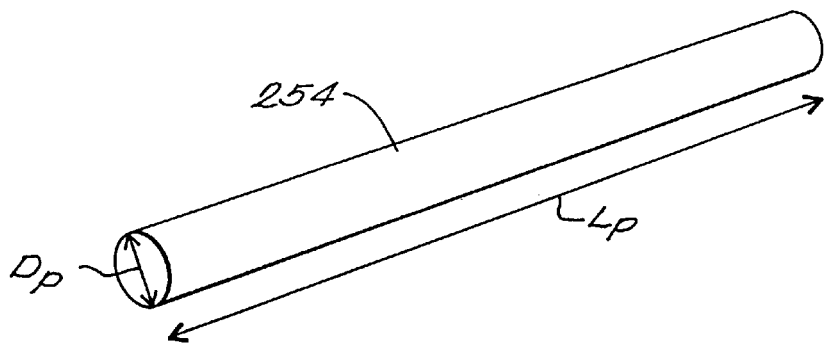
FIG. 4B illustrates a kit for realigning a varus angulated knee having, inter alia, an osteotomy pin for positioning within the cannular opening of the substantially wedge-shaped body illustrated in FIG. 3A, according to an embodiment of the invention.

The present invention also provides an osteotomy pin 254 illustrated in FIG. 4B. Preferably, the osteotomy pin has a length (Lp) ranging from about 50 mm to about 200 mm; and a diameter (Dp) ranging from about 1 mm to about 3 mm. The osteotomy pin 254 can be formed of the same material as the osteotomy device 200.

The osteotomy pin 254 can be placed within the cannular opening 252 of the substantially wedge-shaped body 210 to facilitate the desired placement of the substantially wedge-shaped body 210 at the osteotomy site. For example, a surgeon can insert the osteotomy pin 254 at the osteotomy site. Once the pin is inserted, the surgeon pass the pin 254 into the cannular opening 252 of the substantially wedge-shaped body 210 to guide the placement of the osteotomy device 200 at the osteotomy site. The pin can remain in place to provide additional stability and provide secure attachment for the device 200. Alternatively, the pin 254 can be removed.

The invention further provides a kit for realigning a varus angulated knee which includes the osteotomy device 200 and osteotomy pin 254 described above and illustrated in respective FIGS. 4A and 4B.

In addition, the invention provides a method for realigning a varus angulated knee using a substantially wedge-shaped body having a portion defining a cannular opening along a drive axis and an osteotomy pin. After determining the desired angle of realignment, the surgeon first makes an incision 232 partially into the tibia, leaving the lateral portion 234 of the tibia intact, as illustrated in FIG. 5A. The surgeon realigns the upper portion 236 above the incision 232 and the lower portion 238 below the incision 232 with respect to each other to create a predetermined angle of correction 240 between opposing faces 244, 246 of the incision, as illustrated in FIG. 5B. The lateral intact portion 234 of the tibia serves as a hinge. The separation of the upper 236 and the lower 238 portions of the tibia creates a wedged shaped opening 242. A substantially wedge-shaped body having two principal surfaces angularly offset by the predetermined angle 240 and intersecting to form a vertex is provided. At least one of the principal surfaces of the substantially wedge-shaped body is adapted, at least in part to engage mechanically a surface adjacent thereto.

The surgeon inserts an osteotomy pin 260 at the base 258 of the opening 242, as illustrated in FIG. 5C. Thereafter, the surgeon places a substantially wedge-shaped body 262 having a portion defining a cannular opening 266 within the wedged-shaped opening 242 such that the osteotomy pin 260 is positioned within the cannular opening 266 of the substantially wedge-shaped body 262, as illustrated in FIG. 5D. The osteotomy pin 260 serves as a guide for the placement of the substantially wedge-shaped body 262 into the wedge-shaped opening 242. Axial force is then applied to the drive surface 268 of the substantially wedge-shaped body 262 to drive the body 262 into the wedged-shaped opening 242. At least one of the principal surfaces 282, 284 of the substantially wedge-shaped body 262 mechanically engages adjacent bone material facilitating adherence of the body 262 to the osteotomy site. The body 262 serves to maintain the predetermined angle for a predetermined time period. For example, the body 262 can be formed of a resorbable material selected for its ability to be absorbed into the recipient body over the predetermined time period. This time period can range from about 3 months to about 48 months.

In one embodiment of the invention, the osteotomy device 200 and the osteotomy pin 254 illustrated in FIGS. 4A and 4B, respectively, serve as the respective substantially wedge-shaped body and the osteotomy pin of the method of the invention. Accordingly, at least one of the principal surfaces 212, 214, at least in part, mechanically engages adjacent bone material facilitating adherence of the osteotomy device 200 to the osteotomy site.

In still other embodiments of this method of the invention, cancellous bone is packed into between body and the region between the opposing faces of the incision, like in the method described above. Accordingly, additional cancellous bone can be packed inside a hollow body and such packing facilitated where the body includes holes on its principal surface. Preferably the diameters of such holes can range from about 2 mm to about 10 mm.

The invention may be embodied in other specific forms without departing from the spirit or essential characteristics thereof The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An osteotomy device comprising:
   a substantially wedge-shaped body having two principal surfaces angularly offset by an angle A and intersecting to form a vertex, said principal surfaces extending at least in part about a principal plane from said vertex at an insertion end to a drive surface at a drive end, said principal plane containing a drive axis extending from said vertex toward said drive surface, and said drive surface extending at least in part in a direction transverse to said principal plane, wherein at least one of said principal surfaces is adapted to engage mechanically a surface adjacent thereto, wherein at least one of said principal surfaces is a resorbable material, wherein said drive surface is adapted to receive a force in the direction of said drive axis toward said insertion end, and wherein said substantially wedge-shaped body has a portion defining a cannular opening extending from said vertex along said drive axis.

2. An osteotomy device according to claim 1 wherein at least one of said principal surfaces has a saw-tooth contour along said principal surface.

3. An osteotomy device according to claim 1 wherein said angle A ranges from about 5 degrees to about 25 degrees.

4. An osteotomy device according to claim 1 wherein said substantially wedge-shaped body has a length measured from said insertion end to said drive end ranging from about 20 millimeters to about 100 millimeters.

5. An osteotomy device according to claim 1, wherein said resorbable material is selected from the group consisting of PGA and collagen.

6. An osteotomy device according to claim 1 wherein said resorbable material has a plurality of pores ranging in size from about 50 micrometers to about 500 micrometers.

7. An osteotomy device according claim 1 wherein at least one of said principal surfaces comprises a roughened outer surface.

8. An osteotomy device according to claim 1, wherein said body has a plurality of holes on at least one of said principal surfaces.

9. A kit for realigning a varus angulated knee that comprises:
   A. a substantially wedge-shaped body having two principal surfaces angularly offset by an angle A and intersecting to form a vertex, said principal surfaces extending at least in part about a principal plane from said vertex at an insertion end to a drive surface at a drive end, said principal plane containing a drive axis extending from said vertex toward said drive surface, and said drive surface extending at least in part in a direction transverse to said principal plane, wherein at least one of said principal surfaces is adapted to engage mechanically a surface adjacent thereto, wherein said drive surface is adapted to receive a force in the direction of said drive axis toward said insertion end, and wherein said body has a portion defining a cannular opening along said drive axis extending from said vertex in said principal plane, and
   B. an osteotomy pin for placement within said cannular opening.

10. An osteotomy kit according to claim 9 wherein at least one of said principal surfaces has a saw-tooth contour along said principal surface.

11. An osteotomy kit according to claim 9 wherein said angle A ranges from about 5 degrees to about 25 degrees.

12. An osteotomy kit according to claim 9 wherein said substantially wedge-shaped body has a length measured from said insertion end to said drive end ranging from about 20 millimeters to about 100 millimeters.

13. An osteotomy kit according to claim 9, wherein at least one of said principal surfaces is a resorbable material.

14. An osteotomy kit according to claim 13, wherein said resorbable material is selected from the group consisting of PLA, PGA and collagen.

15. An osteotomy kit according to claim 13 wherein said resorbable material has a plurality of pores ranging in size from about 50 micrometers to about 500 micrometers.

16. An osteotomy kit according claim 9 wherein at least one of said principal surfaces is a nonporous material.

17. An osteotomy kit according claim 16 wherein said non-porous material comprises a roughened outer surface.

18. An osteotomy kit according claim 16 wherein said non-porous material is selected from the group consisting of titanium, graphite and steel.

19. An osteotomy kit according to claim 16 wherein said body has a plurality of holes on at least one of said principal surfaces.

* * * * *